United States Patent [19]

Broekaert et al.

US005773694A

[11] Patent Number: 5,773,694
[45] Date of Patent: Jun. 30, 1998

[54] ANTIMICROBIAL PROTEINS FROM ALLIUM

[75] Inventors: Willem Frans Broekaert, Dilbeek; Bruno Philippe Angelo Cammue, Alsemberg, both of Belgium; Sarah Bronwen Rees, Bracknell, England

[73] Assignee: Zeneca Limited, England

[21] Appl. No.: 591,498

[22] PCT Filed: Jul. 29, 1994

[86] PCT No.: PCT/GB94/01636

§ 371 Date: Jan. 25, 1996

§ 102(e) Date: Jan. 25, 1996

[87] PCT Pub. No.: WO95/04754

PCT Pub. Date: Feb. 16, 1995

[30] Foreign Application Priority Data

Aug. 4, 1993 [GB] United Kingdom .................. 9316158
Aug. 27, 1993 [GB] United Kingdom .................. 9317816

[51] Int. Cl.⁶ ............................. A01H 5/00; A01N 65/00; C07H 21/00; C07K 14/415

[52] U.S. Cl. ................. 800/205; 435/252.3; 435/254.11; 514/12; 530/324; 530/370; 536/23.6

[58] Field of Search ........................... 435/69.1, 32, 243, 435/252.3, 254.11, 419; 514/2, 12; 530/300, 324, 350, 370; 536/23.1, 23.6; 800/205

[56] References Cited

FOREIGN PATENT DOCUMENTS 92 15691 9/1992 WIPO .
92 20801 11/1992 WIPO .

*Primary Examiner*—John L. LeGuyader
*Assistant Examiner*—Thomas G. Larson
*Attorney, Agent, or Firm*—Cushman Darby & Cushman IP Group of Pillsbury Madison & Sutro

[57] ABSTRACT

Antimicrobial proteins capable of isolation from seeds of Allium show a wide range of antifungal activity and some activity against Gram-positive bacteria. DNA encoding the proteins may be isolated and incorporated into vectors. Plants transformed with this DNA may be produced. The proteins find commercial application as antifungal or antibacterial agents; transformed plants will show increased disease resistance.

11 Claims, 7 Drawing Sheets

ELUTION VOLUME(ml)

FIG. 3A

```
                    10              20              30              40           50
Ace-AMP1   QNICPRVNRIVTPCVAYGLGRA--PIA-PCCRALNDLR-FVNTRNLRRAAC
Rs-nsLTP   ALSCGTVNSLNAACIGYLTQNA--PLARGCCTGVTNLNNMA?TTP?????
So-nsLTP   GITCGMVSSKLAPCIGILKGG---PLGGGCCGGIKALNAAAATTPDRKTAC
EP2        VLTCGQVTGALAPCLGYLRSQVNVPVPLTCCNVVRGLNNAARTTLDRKTAC
TobLTP     ALSCGQVQSGLAPCLPYLQGRG--PLG-SCCGGVKGLLGAAKSLSDRKTAC
Le-nsLTP   ALTCGQVTAGLAPCLPYLQGRG--PLG-GCCGGVKNLLGSAKTTADRKTAC
CB-A       -VDCGQVNSSLASCIPFLTGGVASPSA-SCCAGVQNLKTLAPTSADRRAAC
CB-B       -VNCGQVNKALSSCVPFLTGFDTTPSL-TCCAGVMLLKRLAPTVKDKRIAC
CB-C       AVPCSTVDMKAAACVGFATGKDSKPSQ-ACCTGLQQLAQTVKTVDDKKAIC
PAPI       ALNCGQVDSKMKPCLTYVQGGPGGPSG-LCCNGVRDLHNQAQSSGDRQTVC
CW18       AITCGQVSSALGPCAAYAKGSSTSPSA-GCCSGVKRLAGLARSTADKQATC
CW21       AISCGQVSSALSPCISYARGNGAKPPA-ACCSGYKRLAGAAQSTADKQATC
Ta-nsLTP   -IDCGHVDSLVRPCLSYVQGGPG-PSG-QCCDGVKNLHNQARSQSDRQSAC
Zm-nsLTP   AISCGQVASAIAPCISYARGQGSGPSA-GCCSGVRSLNNAARTTADRRAAC
```

FIG. 3B

```
                    60          70          80          90
Ace-AMP1   RCLVGVVNRNPGLRRNPRFQNIPRDCRNTFVRPFWWRPRIQCGRIN
Rs-nsLTP   ?????????????????????????????????????????????
So-nsLTP   NCLKSAANAIKGINYGKAAG-LPGMC-GVHI-PYAISPSTNCNAVH
EP2        GCLKQTANAVTGLNLNAAAG-LPARC-GVNI-PYKISPTTDCNRVV
TobLTP     ICLKSAANAIKGIDMGKAAG-LPGAC-GVNI-PYKISPSTDCSKVQ
Le-nsLTP   TCLKSAANAIKGIDLNKAAG-IPSVC-KVNI-PYKISPSTDCSTVQ
CB-A       ECIKAAAARFPTIKQDAASS-LPKKC-GVDI-NIPISKTTNCQAIN
CB-B       ECVKTAAARYPNIREDAASS-LPYKC-GVVI-NVPISKTTNCHEIN
CB-C       RCLKASSKSL-GIKDQFLSK-IPAAC-NIKV-GFPVSTNTNCETIH
PAPI       NCLKGIARGIHNLNLNNAAS-IPSKC-NVNV-PYTISPDIDCSRIY
CW18       RCLKSVAGAY-NA--GRAAG-IPSRC-GVSV-PYTISASVDCSKIH
CW21       RCIKSAAGGL-NA--GKAAG-IPSMC-GVSV-PYAISASVDCSKIR
Ta-nsLTP   NCLKGIARGIHNLNEDNARS-IPPKC-GVNL-PYTISLNIDCSRV
Zm-nsLTP   NCLKNAAAGVSGLNAGNAAS-IPSKC-GVSI-PYTISTSTDCSRVN
```

FIG. 4A

```
  1 AACGAAAATTACGAAATTACATCAATATCTCGAGCC 37 atgGTTCGCGTTGTATCTTTACTTGCAGCATCGACC
      M   V   R   V   V   S   L   L   A   A   S   T        -16

73 TTCATACTGTTGATTATGATAATCAGCAGTCCGTAT
      F   I   L   L   I   M   I   I   S   S   P   Y         -4

109 GCAAATAGTCAGAACATATGCCCAAGGGTTAATCGA
                ↓
      A   N   S   Q   N   I   C   P   R   V   N   R         +9

145 ATTGTGACACCCTGTGTGGCCTACGGACTCGGAAGG
      I   V   T   P   C   V   A   Y   G   L   G   R        +21

181 GCACCAATCGCCCCATGCTGCAGAGCCCTGAACGAT
      A   P   I   A   P   C   C   R   A   L   N   D        +33

217 CTACGGTTTGTGAATACTAGAAACCTACGACGTGCT
      L   R   F   V   N   T   R   N   L   R   R   A        +45

253 GCATGCCGCTGCCTCGTAGGGGTAGTGAACCGGAAC
      A   C   R   C   L   V   G   V   V   N   R   N        +57
```

FIG. 4B

```
289 CCCGGTCTGAGACGAAACCCTAGATTTCAGAACATT
     P  G  L  R  R  N  P  R  F  Q  N  I     +69
325 CCTCGTGATTGTCGCAACACCTTTGTTCGTCCCTTC
     P  R  D  C  R  N  T  F  V  R  P  F     +81
361 TGGTGGCGTCCAAGAATTCAATGCGGCAGGATTAAC
     W  W  R  P  R  I  Q  C  G  R  I  N     +93
397 CTTACGGATAAGCTTATATACTTGGACGCTGAGGAA
     L  T  D  K  L  U  Y  L  D  A  E  E     +105
433 tgaAGACTAGGCTCTACTGTTATGCACTATAGTTTA
     -
469 TAGTATATATACTAAATAAACAGTATGTGCTGTAT
505 AATTTGCAATATGGACTTATTTATAGCAAGTCCTAA
541 TGGTGTCTGCTACTTGGGTCCAGCATTGAGCACTAT
577 ATAGGCACTATATAGGGTACTATGGGCTGATTATGA
613 TGTCAACGGCGGTACTTTATCTTACATAaataaaTA
649 ATGGGTTTATCTTGCTTGAAAAAAAAAAAAAAAAAA
685 AA
```

ANTIMICROBIAL PROTEINS FROM ALLIUM

This application claims benefit of international application PCT/GB94/01636, filed Jul. 29, 1994.

This invention relates to antimicrobial proteins, processes for their manufacture and use, and DNA sequences coding for them.

In this context, antimicrobial proteins are defined as proteins possessing at least one of the following activities: antifungal activity (which may include anti-yeast activity); antibacterial activity. Activity includes a range of antagonistic effects such as partial inhibition or death. Such proteins may be oligomeric or may be single peptide subunits.

Various proteins with antimicrobial activity have been isolated from plant sources, and such proteins are often believed to take part in host defence mechanisms directed against invading or competing micro-organisms. Some of the proteins are well-characterised, and their amino acid sequence may be known. In some cases, the cDNA or gene encoding the protein has also been isolated and sequenced.

To keep out potential invaders, plants produce a wide array of antifungal compounds, either in a constitutive or an inducible manner. Several classes of proteins with antifungal properties have now been identified, including:

chitinases (Schlumbaum A et al, 1986, Nature, 324, 363–367);

beta-1,3-glucanases (Mauch F et al, 1988, Plant Physiol, 88, 936–942);

chitin-binding lectins (Broekaert WF et al, 1989, Science, 245, 1100–1102; Van Parijs J et al, 1991, Planta, 183, 258–264);

permatins (including zeamatins) (Roberts WK and Selitrennikoff CP, 1990, J Gen Microbiol, 136, 2150–2155; Vigers AJ et al, 1991, Molec Plant-Microbe Interact, 4, 315–323; Woloshuk CP et al, 1991, Plant Cell, 3, 619–628);

thionins (Bohlmann and Apel, 1991, Ann Rev Plant Physiol Plant Mol Biol, 42:227–240);

ribosome-inactivating proteins (Roberts WK and Selitrennikoff CP, 1986, Biosci Rep, 6, 19–29; Leah et al, 1991, J Biol Chem, 266, 1564–1573; Carrasco et al, 1981, Eur J Biochem, 116, 185–189; Vernon et al, 1985, Arch Biochem Biophys, 238, 18–29; Stirpe and Barbieri, 1986, FEBS Lett, 195, 1–8).

These proteins have gained considerable attention as they could potentially be used as biocontrol agents.

Other groups of antimicrobial proteins with activity against plant pathogenic fungi (and often some antibacterial activity) are capable of isolation from certain plant species. We have previously described the structural and antifungal properties of several such proteins, including:

the small-sized cysteine-rich proteins Mj-AMP1 (antimicrobial protein 1) and Mj-AMP2 occurring in seeds of *Mirabilis jalapa* (Cammue BPA et al, 1992, J Biol Chem, 267:2228–2233; International Application Publication Number WO92/15691 published on 17 Sep. 1992);

Ac-AMP1 and Ac-AMP2 from *Amaranthus caudatus* seeds (Broekaert WF et al, 1992, Biochemistry, 37:4308–4314; International Application Publication Number WO92/21699 published on 10 Dec. 1992);

Ca-AMP1 from *Capsicum annuum*, Bm-AMP1 from *Briza maxima* and related proteins found in other plants including Delphinium, Catapodium, Baptisia and Microsensis species (International Patent Application Publication Number WO94/11511, published 26 May 1994);

Rs-AFP1 (antifungal protein 1) and Rs-AFP2 from seeds of *Raphanus sativus* (Terras FRG et al, 1992, J Biol Chem, 267:15301-13309) and related proteins such as Bn-AFP1 and Bn-AFP2 from *Brassica napus*, Br-AFP1 and Br-AFP2 from *Brassica rapa*, Sa-AFP1 and Sa-AFP2 from *Sinapis alba*, At-AFP1 from *Arabidopsis thaliana*, Dm-AMP1 and Dm-AMP2 from *Dahlia merckii*, Cb-AMP1 and Cb-AMP2 from *Cnicus benedictus*, Lc-AFP from *Lathyrus cicera*, Ct-AMP1 and Ct-AMP2 from *Clitoria ternatea* (International Patent Application Publication Number WO93/05153 published 18 Mar. 1993).

These publications are specifically incorporated herein by reference.

These and other plant-derived antimicrobial proteins are useful as fungicides or antibiotics to improve the disease-resistance or disease-tolerance of crops either during the life of the plant or for post-harvest crop protection. The proteins may be extracted from plant tissue or produced by expression within micro-organisms or synthesised. Exposure of a plant pathogen to an antimicrobial protein may be achieved by application of the protein to plant parts using standard agricultural techniques (eg surface spraying). The proteins may also be used to combat fungal or bacterial disease by expression within plant bodies (rather than just at the surface). The antimicrobial protein may be expressed in an endophyte introduced into plant tissue. DNA encoding the antimicrobial proteins (which may be a cDNA clone, a genomic DNA clone or DNA manufactured using a standard nucleic acid synthesiser) may also be transformed into a plant, and the proteins expressed within transgenic plants. For example, transgenic tobacco expressing a barley ribosome inactivating protein has increased resistance to the fungal pathogen *Rhizoctonia solani* (Logemann et al, 1992, Biotechnol, 10:305–308); transgenic tobacco expressing a barley α-thionin has increased resistance to Pseudomonas bacterial pathogens (Carmona et al, 1993, Plant J, 3(3):457–462); transgenic tobacco expressing a bean chitinase has increased resistance to the fungal pathogen *Rhizoctonia solani* (Broglie et al, 1991, Science, 254:1194–1197).

Another group of plant proteins have recently been linked to a potential role in plant defence. Non-specific lipid transfer proteins (hereinafter referred to as nsLTPs) are a family of proteins of unknown function, which are classified as lipid transfer proteins based on their ability to shuttle phospholipids between membrane vesicles or organelles in vitro. These proteins are able to translocate phospholipids or other apolar compounds between two membrane systems. Non-specific lipid transfer proteins have been isolated from both mono- and dicotyledonous species, including;

*Spinacia oleracea* (So-nsLTP; Bernhard WR et al, 1990, Plant Physiol, 95:164–170);

*Ricinus communis* (CB-A, CB-B and CB-C; Takishima K et al, 1988, Eur J Biochem, 190:107–112);

*Daucus carota* (Dc-nsLTP or EP2; Sterk et al, 1991, Plant Cell, 9:907–921);

*Nicotiana tabacum* (TobLTP; Masuta C et al, 1992, FEBS Lett; 311: 119–123);

*Hordeum vulgare* (PAPI, Mundy J and Rogers JC, 1986, Planta, 169: 51–63));

*Zea mays* (Zm-nsLTP; Tchang F et al, 1988, J Biol Chem, 263:16849–16855).

These proteins were previously thought to play a role in cytoplasmic lipid shuttling between organelles, that is the transport of phospholipids from endoplasmic reticulum to cell and organelle membranes (Arondel V and Kader JC, 1990, Experientia, 46, 579–585). However, recent evidence shows that at least some nsLTPs are located extra-cellularly, making their proposed function in membrane biogenesis unlikely (Sterk P et al, 1991, Plant Cell, 3, 907–921; Thoma S et al, 1993, Plant J, 3:427–436).

We have previously described an antimicrobial protein isolated from radish seeds, designated Rs-nsLTP (*Raphanus sativus* non-specific lipid transfer protein) because of its homology with non-specific lipid transfer proteins isolated from other plant species (International Patent Application Publication Number WO93/05153 published on 18 Mar. 1993). Rs-nsLTP inhibits the growth of several fungi in vitro and shows 38 to 53% sequence identity with a variety of non-specific lipid transport proteins from other plant sources. We have therefore proposed a model in which nsLTPs play a role in defence against microbial attack (Terras FRG et al, 1992, Plant Physiol, 100:1055–1058).

Molina A et al (1993, FEBS Letters, 316(2):119–122) isolated four homogeneous proteins (CW18, CW20, CW21, CW22) from barley leaves which inhibited growth of the pathogens *Clavibacter michiganensis* subsp. sepedonicus, *Pseudomonas solanacearum* and *Fusarium solani*. The amino acid sequences of these proteins were homologous to known nsLTPs from plants (32–62% identical positions). A homologous protein ($Cw_{41}$) was purified from maize leaves and also found to have inhibitory properties. Molina et al therefore proposed a defence role for non-specific lipid transfer proteins from plants. International Patent Application Publication Number WO92/20801 (Universidad Politecnica de Madrid; published on 26 Nov. 1992) discusses the antipathogenic activity (particularly antibacterial activity) of phospholipid transfer proteins (particularly the barley proteins CW18, CW20, CW21 AND CW22), antipathogenic compositions containing such proteins, DNA sequences encoding such proteins and transgenic plants expressing such proteins.

We have now identified novel potent antimicrobial proteins with broad spectrum activity against plant pathogenic fungi and with some antibacterial activity.

According to the present invention, there is provided an antimicrobial protein having substantially the amino acid sequence shown in SEQ ID NO 1.

An antimicrobial protein according to the invention is capable of isolation from seeds of the family Alliaceae, in particular from the genus Allium. Such proteins may also be isolated from the seeds of both related and unrelated species, or may be produced or synthesised by any suitable method.

The invention further provides a DNA sequence encoding a protein according to the invention, and a vector containing said sequence. The DNA may be cloned or transformed into a biological system allowing expression of the encoded protein.

In a further aspect, the invention provides plants transformed with DNA encoding an antimicrobial protein according to the invention.

The invention further provides a process of combating fungi or bacteria whereby they are exposed to the proteins according to the invention.

An antimicrobial protein according to the invention has been isolated from seeds of *Allium cepa* (onion) and is hereinafter called Ace-AMP1 (*Allium cepa*—Antimicrobial Protein 1). Ace-AMP1 shows activity against a range of plant pathogenic fungi.

The amino acid sequence of the Ace-AMP1 protein has been determined by direct sequencing of the protein and by translation of the full-length Ace-AMP1 cDNA sequence. Ace-AMP1 has a unique primary structure. Although it is partially homologous to non-specific lipid transfer proteins (nsLTPs) from various plant sources, Ace-AMP1 is distinguished from the nsLTPs in several ways. Ace-AMP1 deviates at 22% of the positions where all known nsLTPs share conserved residues. In contrast to nsLTPs, Ace-AMP1 is extremely rich in arginine (19 arginines in 93 residues; approximately 20% of amino acid content is arginine). As discussed above, some nsLTPs have shown antimicrobial activity. However, the antimicrobial activity of Ace-AMP1 is considerably stronger than that of nsLTPs (see comparative tests in Example 7). Ace-AMP1 shows a particularly strong antifungal activity and a particularly broad spectrum of antifungal activity. Moreover, the antimicrobial activity of Ace-AMP1 is significantly higher than that of the nsLTPs when assessed in the presence of inorganic cations at physiological concentrations. In addition, Ace-AMP1 appears to have no lipid transfer activity: tests have shown that, in contrast to nsLTPs like those isolated from maize or wheat seeds, Ace-AMP1 was unable to transfer phospholipids from liposomes to mitochondria. As a further distinction, the structure of the cDNA clone encoding Ace-AMP1 has a preproprotein structure whereas cDNA encoding known nsLTPs has a preprotein structure (see Examples 9, 10 and 11).

An antimicrobial protein according to the invention is a protein having antifungal activity and having an amino acid sequence substantially as shown in SEQ ID NO 1. In particular, an antimicrobial protein according to the invention is rich in arginine.

Knowledge of its primary structure enables manufacture of the antimicrobial protein, or parts thereof, by chemical synthesis using a standard peptide synthesiser. It also enables production of DNA constructs encoding the antimicrobial protein. The DNA sequence may be predicted from the known amino acid sequence or the sequence may be isolated from plant-derived DNA libraries.

Oligonucleotide probes may be derived from the known amino acid sequence and used to screen a cDNA library for cDNA clones encoding some or all of the protein. These same oligonucleotide probes or cDNA clones may be used to isolate the actual antimicrobial protein gene(s) by screening genomic DNA libraries. Such genomic clones may include control sequences operating in the plant genome. Thus it is also possible to isolate promoter sequences which may be used to drive expression of the antimicrobial (or other) proteins. These promoters may be particularly responsive to environmental conditions (such as the presence of a fungal pathogen), and may be used to drive expression of any target gene.

The Ace-AMP1 cDNA has been isolated using PCR-based cloning as described in Example 9.

DNA encoding the antimicrobial protein (which may be a cDNA clone, a genomic DNA clone or DNA manufactured using a standard nucleic acid synthesiser) can then be cloned into a biological system which allows expression of the protein or a part of the protein. The DNA may be placed under the control of a constitutive or inducible promoter. Examples of inducible systems include pathogen induced expression and chemical induction. Hence the protein can be produced in a suitable micro-organism or cultured cell, extracted and isolated for use. Suitable micro-organisms include *Escherichia coli*, Pseudomonas and yeast. Suitable cells include cultured insect cells and cultured mammalian cells. The genetic material can also be cloned into a virus or bacteriophage. The DNA can also be transformed by known methods into any plant species, so that the antimicrobial protein is expressed within the plant.

Plant cells according to the invention may be transformed with constructs of the invention according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocotyledonous and dicotyledonous plants may be obtained in this way.

Examples of genetically modified plants which may be produced include field crops, cereals, fruit and vegetables such as: oilseed rape, canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The antimicrobial proteins of the invention show surprisingly high activity and inhibit the growth of a variety of plant pathogenic fungi at submicromolar doses. The proteins not only show a wide range of antifungal activity but also activity against Gram positive bacteria. The proteins are thus useful as fungicides or antibiotics, for agricultural or pharmaceutical applications. Exposure of a plant pathogen to an antimicrobial protein may be achieved by expression of the protein within a micro-organism (including an endophyte) which is applied to a plant or the soil in which a plant grows. The proteins may also be used to combat fungal or bacterial disease by application of the protein to plant parts using standard agricultural techniques (eg spraying). An antimicrobial composition may comprise an antimicrobially effective amount of the protein together with an agriculturally acceptable carrier and/or adjuvant customarily used in agricultural protein formulations (including solid or liquid adjuvants, solvents, surfactants, etc). The proteins may also be used to combat fungal or bacterial disease by expression within plant bodies, either during the life of the plant of for post-harvest crop protection. The protein may also be used as a fungicide or anti-bacterial to treat mammalian infections, or for preservation of products susceptible to contamination by micro-organisms (for example, processed food products).

The antimicrobial proteins may be isolated and purified from appropriate seeds, synthesised artificially from their known amino acid sequence, or produced within a suitable micro-organism by expression of recombinant DNA. The proteins may also be expressed within a transgenic plant.

BRIEF DESCRIPTION OF THE DRAWINGS

The invention may be further understood by reference to the drawings, in which:

FIGS. 3A and 3B show the alignment of the amino acid sequences of Ace-AMP1 and various plant non-specific lipid transfer proteins (SEQ ID NOS: 1–14).

FIGS. 4A and 4B show the sequences of the Ace-AMP1 cDNA (SEQ ID NO: 15) and translated protein (SEQ ID NO: 16).

Figure 1A:
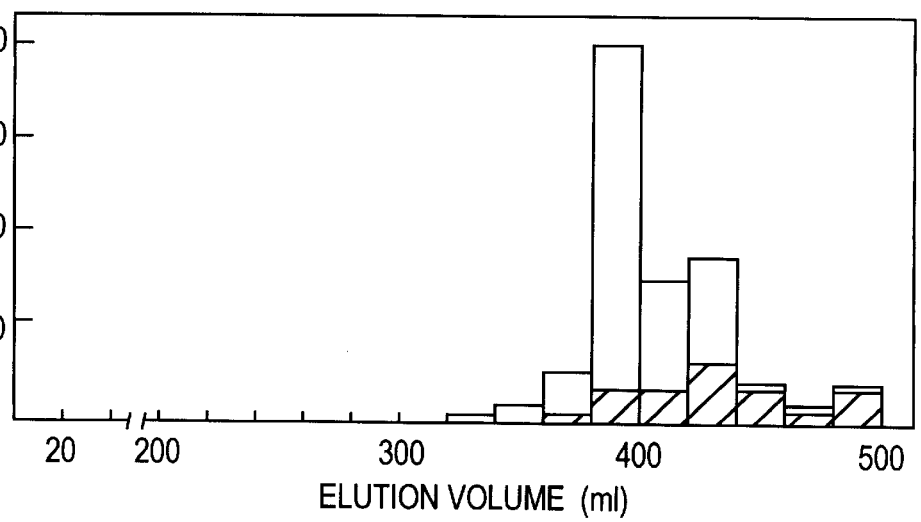
FIGS. 1A and 1B show the cation exchange chromatogram for Ace-AMP1 and the associated graph of fungal growth inhibition.

The invention may also be further understood by reference to the Sequence Listing, in which:

SEQ ID NOs 1 to 14 refer to the amino acid sequences in FIGS. 3A and 3B:
SEQ ID NO 1 is mature Ace-AMP1;
SEQ ID NO 2 is Rs-nsLTP;
SEQ ID NO 3 is So-nsLTP;
SEQ ID NO 4 is EP2;
SEQ ID NO 5 is TobnsLTP;
SEQ ID NO 6 is Le-nsLTP;
SEQ ID NO 7 is CB-A;
SEQ ID NO 8 is CB-B;
SEQ ID NO 9 is CB-C;
SEQ ID NO 10 is PAPI;
SEQ ID NO 11 is CW18;
SEQ ID NO 12 is CW21;
SEQ ID NO 13 is Ta-nsLTP;
SEQ ID NO 14 is Zm-nsLTP;

SEQ ID NOs 15 to 16 refer to the sequences in FIGS. 4A and 4B:
SEQ ID NO 15 is the nucleic acid sequence of the Ace-AMP1 cDNA;
SEQ ID NO 16 is the amino acid sequence of Ace-AMP1 translated from the cDNA sequence;

SEQ ID NOs 17 to 25 refer to the oligonucleotides listed in Table 5;
SEQ ID NO 17 is OWB114;
SEQ ID NO 18 is OWB116;
SEQ ID NO 19 is OWB117;
SEQ ID NO 20 is OWB111;
SEQ ID NO 21 is OWB132;
SEQ ID NO 22 is OWB133;
SEQ ID NO 23 is OWB158;
SEQ ID NO 24 is OWB159;
SEQ ID NO 25 is OWB160.

The following Examples illustrate the invention.

EXAMPLE 1

Antifungal and Antibacterial Activity Assays.

Antifungal activity was measured by microspectrophotometry as previously described (Broekaert, 1990, FEMS Microbiol Lett, 69:55–60). Routinely, tests were performed with 20 µl of a (filter-sterilized) test solution and 80 µl of a suspension of fungal spores ($2 \times 10^4$ spores/ml) in either half strength potato dextrose broth (medium A) or half strength potato dextrose broth with $CaCl_2$ and KCl added to final concentrations of 1 mM and 50 mM respectively (medium B).

For experiments on the antagonistic effect of cations, a synthetic growth medium was used. The synthetic growth medium consisted of $K_2HPO_4$ (2.5 mM), $MgSO_4$ (50 µM), $CaCl_2$ (50 µM), $FeSO_4$ (5 µM), $CoCl_2$ (0.1 µM), $CuSO_4$ (0.1 µM), $Na_2MoO_4$ (2 µM), $H_3BO_3$ (0.5 µM), KI (0.1 µM), $ZnSO_4$ (0.5 µM), $MnSO_4$ (0.1 µM), glucose (10 g/l), asparagine (1 g/l), methionine (20 mg/l), myo-inositol (2 mg/l), biotin (0.2 mg/l), thiamine-HCl (1 mg/l), and pyridoxine-HCl (0.2 mg/l).

Unless otherwise stated the test organism was *Fusarium culmorum* (strain IMI 180420) and incubation was done at 25° C. for 48 hours. The antifungal activity of a sample (units per ml) is defined as the total volume of the assay mixture divided by the volume of the sample in the assay mixture that gives 50 percent growth inhibition (=dilution factor for 50 percent growth inhibition). Percent growth inhibition is defined as 100 times the ratio of the corrected absorbance of the control microculture minus the corrected absorbence of the test microculture over the corrected absorbence at 595 nm of the control microculture. The corrected absorbence values equal the absorbence at 595 nm of the culture measured after 48 hours minus the absorbence at 595 nm measured after 30 min.

Antibacterial activity was measured microspectrophotometrically as follows. Bacteria were pre-cultured overnight in 2% Tryptone at 30° C. in a rotary shaker. A soft agarose medium (2% tryptone; 0.5% low melting point agarose) was inoculated with the bacteria to a cell density of $10^5$ colony forming units/ml). Aliquots (80 µl) of the bacterial suspension were added to filter-sterilized samples (20 µl) in flat-bottom 96-well microplates and allowed to solidify. The absorbence at 595 nm of the culture was measured with the aid of a microplate reader after 30 minutes and 24 hours of incubation at 28° C. Percent growth inhibition was calculated as described above for the antifungal activity assay.

Antibiotic activity on yeast was determined as for the antibacterial assay, except that the growth medium consisted of half strength potato dextrose broth (Difco) and 0.5% low melting point agarose. Eighty µl of a suspension of yeast cells in the latter medium ($10^6$ cells/ml) was added to 20 µl of the test solution.

EXAMPLE 2

Extraction of basic heat-stable proteins from *Allium cepa* seeds

One hundred grammes of *Allium cepa* seeds (from AVEVE, Belgium) were ground in a coffee mill and the resulting meal was extracted for 2 hours at 4° C. with 200 ml of an ice-cold extraction buffer containing 10 mM $NaH_2PO_4$, 15 mM $Na_2HPO_4$, 100 mm KCl, 2 mM EDTA and 2 mM thiourea. After extraction, the slurry was mixed in a WARING blender and subsequently squeezed through a jam mincer to separate the extract from the solid residue. The resulting extract was clarified by centrifugation (10 min at 5,000× g). Solid ammonium sulphate was added to the supernatant to obtain 85% relative saturation and the precipitate allowed to form by standing overnight at 4° C. Following centrifugation at 7,000× g for 30 minutes, the precipitate was redissolved in 100 ml distilled water and dialyzed extensively against distilled water. After dialysis the solution was adjusted to 50 mM $NH_4Ac$ (pH 9) by addition of the ten-fold concentrated buffer and passed over a Q-Sepharose Fast Flow (Pharmacia, Uppsala, Sweden) column (12×5 cm) equilibrated in 50 mM $NH_4Ac$ (pH 9). The protein fraction which passed through the column was lyophilised and redissolved in 200 ml 50 mM $NH_4Ac$ (pH 5.5).

This material represents the basic (pI>9) protein fraction of the seeds. This fraction was further purified as described in Example 3.

EXAMPLE 3

Purification of an antimicrobial protein from *Allium cepa* seeds

The starting material for the isolation of the *Allium cepa* antimicrobial protein was the basic protein fraction extracted from the mature seeds as in Example 2. Proteins were further purified by cation exchange chromatography of this extract.

Figure 1B:
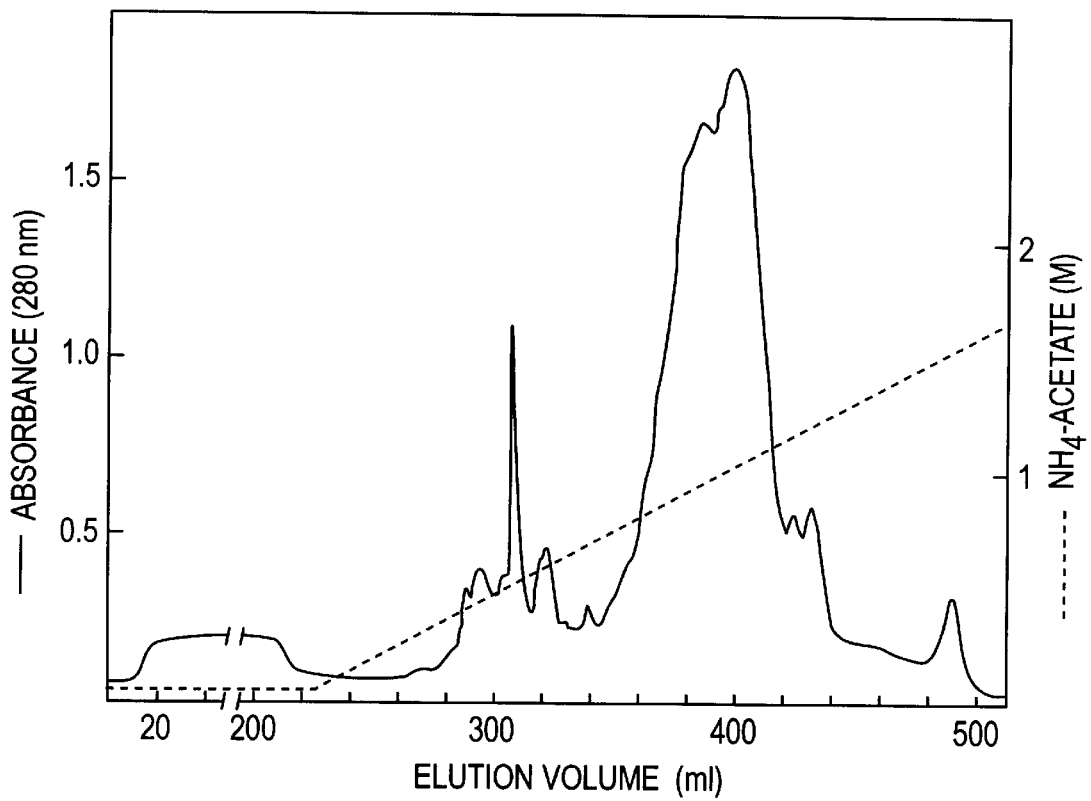

Approximately 200 ml of the basic protein fraction was applied to a S-Sepharose High Performance (Pharmacia) column (10×1.6 cm) equilibrated in 50 mM $NH_4Ac$, pH 5.5. The column was eluted at 2.0 ml\min with a linear gradient from 50 mM to 2M $NH_4Ac$, pH 5.5 over 180 minutes. The eluate was monitored for protein by online measurement of the absorbence at 280 nm (results shown in FIG. 1B) and collected in 20 ml fractions. One ml samples from each fraction were dried by lyophilisation, and redissolved in 1 ml of distilled water of which 20 µl was assayed for antifungal activity as described in Example 1 (Results shown in FIG. 1A) in both medium A and B.

Figure 2A:
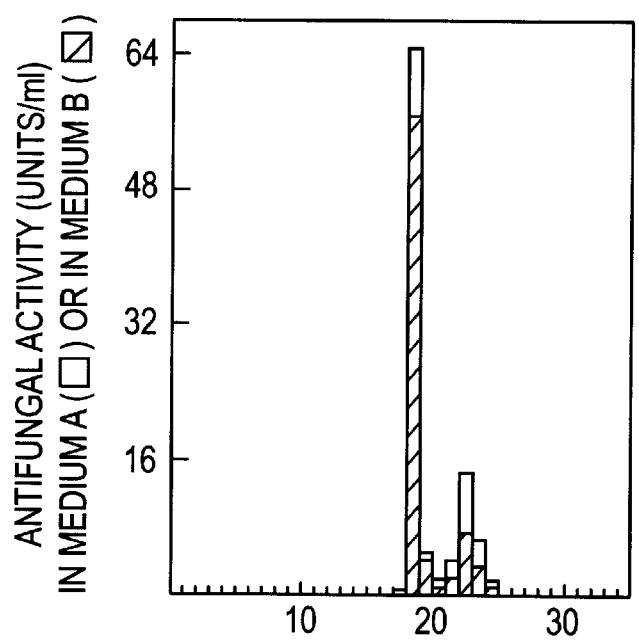
FIGS. 2A and 2B show the HPLC profile of purified Ace-AMP1.
Figure 2B:
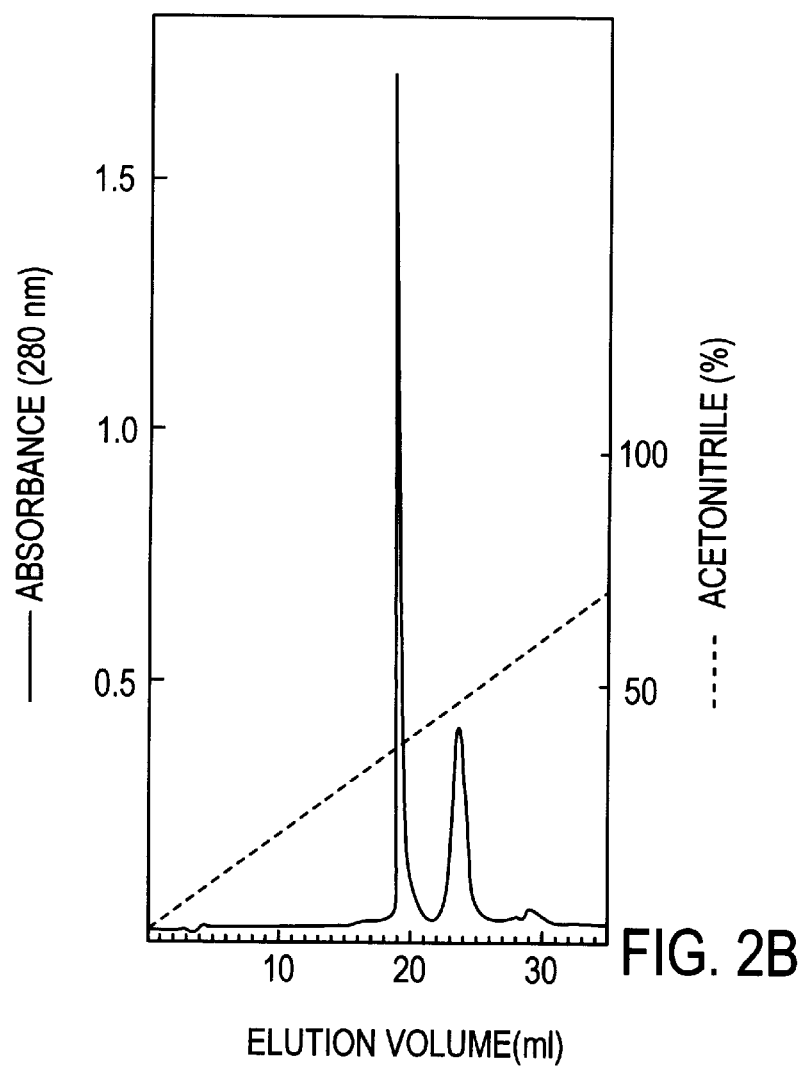

Following chromatography, the extract yielded a broad and complex peak of antifungal activity, composed of at least two active components with different sensitivity to presence of $CaCl_2$ and KCl in the assay medium (Medium B) and a well-defined active peak eluting at approximately 1.5M $NH_4$-acetate. The latter peak, being the less antagonised by $Ca^{2+}$ and $K^+$ could be further purified by reverse-phase HPLC. One ml of this peak fraction was loaded on a PEP-S (porous silica $C_2/C_{18}$, Pharmacia) column (25×0.4 cm) equilibrated with 0.1% TFA (trifluoracetic acid). The column was developed at 1 ml/min with a linear gradient of 0.1% TFA to 100% acetonitrile/0.1% TFA over 50 minutes. The eluate was monitored for protein by online measurement of the absorption at 280 nm (results shown in FIG. 2B). One ml fractions were collected, vacuum dried, and redissolved in 1 ml distilled water of which 20 µl was used in an antifungal assay as described in Example 1 (results shown in FIG. 2A). The first single well-resolved peak of activity was called Ace-AMP1 (*Allium cepa*—Antimicrobial Protein 1).

EXAMPLE 4

Molecular structure of the purified antimicrobial protein, Ace-AMP1

The molecular structure of the purified antimicrobial protein was further analysed. Sodium dodecyl sulphate polyacrylamide gel electrophoresis (SDS-PAGE) was performed on precast commercial gels (PhastGel 8–25% from Pharmacia) using a PhastSystem (Pharmacia) electrophoresis apparatus. The sample buffer contained 200 mM Tris-HCl (pH 8.3), 1% (w/v) SDS, mM EDTA, 0.005% bromophenol blue and, unless otherwise stated, 1% (w/v) dithioerythritol (DTE). Proteins were fixed after electrophoresis in 12.5% glutaraldehyde and silver-stained according to Heukeshoven and Dernick (1985, Electrophoresis, 6:103–112). Molecular weight markers run for comparison were: phosphorylase B (97.4 kDa), bovine serum albumin (66.2 kDa), ovalbumin (42.7 kDa), carbonic anhydrase (31.0 kDa), soybean trypsin-inhibition (21.5 kDa) and lysozyme (14.4 kDa).

SDS-PAGE analysis of reduced and unreduced Ace-AMP1 revealed a single band of approximately 10 kDa and 22 kDa, respectively. The molecular weight of about 10 kDa of the reduced Ace-AMP1 could be confirmed by a similar SDS-PAGE on PhastGel High Density (Pharmacia) which allows increased resolution for proteins below 20 kDa. Determination of the molecular mass of native Ace-AMP1 by gel filtration on Superose-12 (Pharmacia) yielded a value of about 7.5 kDa. The SDS-PAGE molecular mass value of 22 kDa for unreduced Ace-AMP1 may be an overestimation due to a relatively low SDS binding capacity of this compact protein.

Determination of covalently bound sugars using the phenol-sulphuric acid method of Dubois et al (1956, Anal Chem, 28:350–356) and D-glucose as a standard, was negative, suggesting that Ace-AMP1 is not glycosylated.

All cysteine residues of Ace-AMP1 appeared to participate in disulphide bonds, as unreduced Ace-AMP1 did not contain free thiol groups. Thiol group determination was done by the dithionitrobenzoic acid method of Ellman, GL (1959; Arch Biochem Biophys, 82:70–74) using 10 ml of protein. Reduced protein samples were prepared by reaction with 10 mM DTT for 1 hour at 45° C. followed by extensive dialysis against distilled water.

EXAMPLE 5

Amino acid sequencing of Ace-AMP1

Cysteine residues were modified by S-carboxyamidomethylation as described in Cammue BPA et al, 1992, J Biol Chem, 267:2228–2233. Reagents were removed by HPLC on a Pep-S (porous silica $C_2/C_{18}$) (Pharmacia) column (25×0.4 cm). The S-carboxyamidomethylated proteins were recovered by eluting the column with a linear gradient from 0.1% trifluoracetic acid (TFA) to acetonitrile containing 0.1% TFA. The resulting protein fractions were subjected to amino acid sequence analysis in a 477A Protein Sequence (Applied Biosystems) with on-line detection of phenylthiohydantoin amino acid derivatives in a 120A Analyser (Applied Biosystems).

Initial attempts to sequence Ace-AMP1 showed that the protein was N-terminally blocked. Since deblocking with pyroglutamate amino peptidase (Boehringer, FRG) was unsuccessful, Ace-AMP1 was digested with the endoproteinases Arg-C and Asp-N (both of sequencing grade from Boehringer, FRG). Digestion was done according to the manufacturers' instructions on reduced and S-carboxyamidomethylated Ace-AMP1 applying minimal advised enzyme to protein ratios (w/w) and maximal advised incubation times. Digested peptides were subsequently separated by RP-HPLC on a Pep-S (porous silica $C_2/C_{18}$; Pharmacia) column (25×0.4 cm) using a linear elution gradient from 0.1% TFA to acetonitrile containing 0.1% TFA in 100 minutes at 1 ml/minute. Digestion with Arg-C resulted in at least 10 separable peptides, suggesting already a relatively high arginine content of Ace-AMP1. Treatment with Asp-N generated 3 protein fragments. After sequencing of these peptides the primary structure of Ace-AMP1 was reconstructed with exception of the blocked N-terminal part.

The Ace-AMP1 amino acid sequence was found to be partially homologous with non-specific lipid transfer proteins (nsLTPs) from different plant sources, including: Rs-nsLTP from *Raphanus sativus* seeds (Terras FRG et al, 1992, Plant Physiology; 100: 1055–1058); So-nsLTP from *Spinacia oleraceae* leaves (Bernhard WR et al, 1991, Plant Physiology, 95: 164–170); EP2 from *Daucus carota* zygotic embryos (Sterk P et al, 1991, Plant Cell, 3:907–921); TobLTP from *Nicotiana tabacum* flowers (Masuta C et al, 1992, FEBS Lett; 311:119–123); Le-nsLTP from *Lycopersicon esculente* (Tonnes-Schumann S et al, 1992, Plant Mol Biol, 18:749–757); CB-A, CB-B and CB-C from *Ricinus communis* seedlings (Takishima K et al, 1988, Eur J Buiochem, 190:1070112); PAPI from *Hordeum vulgare* seeds (Mundy J and Rogers JC, 1986, Planta, 169:51–63); CW18 and CW21 from *Hordeum vulgare* leaves (Molina A et al, 1993, FEBS Lett, 316:119–122); Ta-nsLTP from *Triticum aestivum* (Simorre JP et al, 1991, Biochem, 30:11600–11608); Zm-nsLTP from *Zea mays* seedlings (Tchang F et al, 198, J Biol Chem, 263: 16849–16855). A sequence comparison of Ace-AMP1 with these nsLTPs is given in FIGS. 3A and 3B. Gaps introduced for optimal alignment are represented by dashes. The first nine N-terminal amino acids are derived from the nucleotide sequence of Ace-AMP1 cDNA (see Example 5).

From a comparison of the nsLTP sequences shown in FIGS. 3A and 3B (all sequences excluding Ace-AMP1), the following consensus motif can be derived. All eight cysteines are at conserved positions 4, 14, 30, 31, 51, 53, 77 and 93 (numbering as in FIG. 3); hydrophobic residues (L, I, A, V, M) or aromatic residues (F, W, Y) appear at positions 2, 7, 11, 17, 18, 34, 37, 41, 54, 61, 64, 69, 73, 82, 85, 87, and 96; prolines are present at positions 25 and 74; basic residues (H, R, K) are conserved at positions 47 and 55; hydroxy residues (S, T) appear at positions 43 and 88; and a conserved aspartic acid occupies position 46. Ace-AMP1 partly corresponds to this consensus motif, but deviates at the following positions: it does not have hydrophobic/aromatic residues at positions 2, 18, 61 and 69; it does not have the conserved aspartic acid, lysine and serine at positions 46, 55 and 88 respectively. Hence, about 22% of the conserved residues in nsLTP proteins are altered in Ace-AMP1. Moreover, Ace-AMP1 distinguishes itself from all other known nsLTP sequences by a much higher arginine content. Ace-AMP1 contains at least 19 arginines whereas the number of arginines in the nsLTP proteins varies from 1 (So-nsLTP) to 6 (Zm-nsLTP).

It is noted that most cysteine-rich antibiotic peptides found in animals, such as defensins (Lehrer RI et al, 1991, Cell, 64:229–230), β-defensins (Selsted ME et al, 1993, J Biol Chem, 268:6641–6648) and bactenecins (Romeo D et al, 1988, J Biol Chem, 263:9573–9575; Gennaro R et al, 1989, Infect immun, 57:3142–3146) are also particularly rich in arginine.

EXAMPLE 6

Stability of the protein's antifungal activity

Table 1 summarises the results of further testing of the stability of the antifungal activity of Ace-AMP1.

Tests for antifungal activity were performed with 20 µl samples diluted five-fold with growth medium containing *Fusarium culmorum* spores, according to the assay method given in Example 1. Untreated control samples consisted of the test proteins at 100 µg/ml in 10 mM sodium phosphate buffer (pH 7). Heat stability tests were performed by heating aliquots of the test proteins for 10 minutes at different temperatures up to 100° C. For digestions, proteases were added at 400 µg/ml and incubated at 37° C. for 16 hours.

TABLE 1

Stability of the antifungal activity of Ace-AMP1

| Treatment | Relative antifungal activity (% of control activity) |
| --- | --- |
| Control | 100 |
| Heating at 80° C., 10 min | 100 |
| Heating at 90° C., 10 min | 100 |
| Heating at 100° C., 10 min | 100 |
| Chymotrypsin digestion | 80 |
| Pronase E digestion | 5 |
| Proteinase K digestion | 60 |
| Trypsin digestion | 90 |

The antifungal activity of Ace-AMP1 was not affected by heat treatments up to 100° C. for 10 minutes. Ace-AMP1 was relatively resistant to treatments with chymotrypsin, trypsin and proteinase K while digestion with pronase E reduced the activity almost completely.

EXAMPLE 7

Antifungal potency of Ace-AMP1

The antifungal potency of the purified protein was assessed on different plant pathogenic fungi, using the assay described in Example 1. Growth of fungi, collection and harvest of fungal spores were done as previously described (Broekaert et al, 1990, FEMS Microbiol Lett, 69:55–60). The following fungal strains were used: *Alternaria brassicola* MUCL 20297, *Ascochyta pisi* MUCL 30164, *Botrytis cinerea* MUCL 30158, *Colletotrichum lindemuthianum* MUCL 9577, *Fusarium culmorum* IMI 180420, *Fusarium oxysporum* f.sp. in IMI 236441, *Fusarium oxysporum* f.sp. lycopersici MUCL 909, *Nectria haematococca* Collection Van Etten 160-2-2, *Phoma betae* MUCL 9916, *Pyrenophora tritici-repentis* MUCL 30217, *Pyricularia oryzae* MUCL 30166. *Verticillium dahliae* MUCL 6963.

Serial dilutions of the antifungal proteins were applied to the fungi, using a synthetic growth medium for fungi (SMF) (See Example 1) supplemented with (SMF$^+$) or without (SMF$^-$) CaCl$_2$ and KCl to final concentrations of 1 mM and 50 mM, respectively. The percent growth inhibition was measured by microspectrophotometry. The concentration required for 50% growth inhibition after 48 h of incubation (IC$_{50}$ value) was calculated from the dose-reponse curves.

The IC$_{50}$ values of Ace-AMP1 on different plant pathogenic fungi are presented in Table 2, where they are compared with those determined under the same conditions for three nsLTPs, namely Rs-nsLTP (data from Terras et al, 1992, Plant Physiol. 100:1055–1058), Zm-nsLTP and Ta-nsLTP (isolated as described in Simorre et al, 1991, Biochem, 30:11600–11608).

Both in media SMF– and SMF+, Ace-AMP1 inhibits all twelve tested fungi by 50% at concentrations equal or below 10 μg/ml (corresponding to about 1 μM). Ace-AMP1 is therefore a potent plant antifungal protein exhibiting a broad inhibitory spectrum.

It is surprising that Ace-AMP1 is almost as active in SMF$^+$ as in SMF$^-$. The activity of an antifungal protein in a cation containing medium such as SMF$^+$ is believed to be of physiological relevance since all plant cell compartments contain relatively high cation concentrations (Terras FRG et al, 1992, J Biol Chem, 267:15301–15309).

The potency of Ace-AMP1 in SMF$^+$ compares very favourable to other relatively cation-insensitive antifungal proteins such as Rs-AFP2 which inhibits 8 out of 12 fungi listed in Table 2 at concentrations below 10 μg/ml (Terras FG et al, 1992, J Biol Chem, 267:15301–15309). Ace-AMP1 is also much more potent than a recently described nsLTP-like protein from *Raphanus sativus*, Rs-nsLTP (Terras FRG et al, 1992, Plant Physiol, 100:1055–1058) which is partly homologous to Ace-AMP1 (see FIGS. 3A and 3B). Indeed, none of the fungi listed in Table 2 are inhibited by Rs-nsLTP in SMF$^+$ at concentrations below 100 μg/ml (Terras FRG et al, 1992, Plant Physiol, 100:1055–1058). Moreover, two nsLTPs isolated from maize and wheat, Zm-nsLTP and Ta-nsLTP respectively, did not inhibit growth of any of the nine fungi tested in SMF+ at concentrations below 200 EMG/ML (see Table 2). The IC$_{50}$ value on *Fusarium solani* of nsLTP proteins isolated from barley leaves (including CW18 and CW21, see FIGS. 3A and 3B) varied from approximately 25 to 180 μg/ml (depending on the isoform) when assessed in potato dextrose broth as a medium (Molina A et al, 1993, FEBS Lett, 316:119–122). However, the activity of these proteins on other fungi and their sensitivity to cations have not been described.

The activity of Ace-AMP1 on *Fusarium culmorum* in synthetic growth medium supplemented with different cations (assayed as described in Example 1) has been compared directly with the activity of the Ac-AMP1 antimicrobial peptide from *Amaranthus caudatus* seeds (Broekaert et al, 1992, Biochemistry, 31: 4308–4314) and of β-purothionin from wheat endosperm (another type of plant seed protein with antimicrobial activity; Redman DG and Fischer N, 1969, J Sci Food Agri, 20: 427–432). Table 3 summarises the IC$_{50}$ values under different conditions. Whereas Ac-AMP1 is very sensitive to the presence of all tested cations, the activities of Ace-AMP1 and β-purothionin seem to be rather cation-stimulated although not by Ca$^{2+}$. The antagonistic effect of Ca$^{2+}$ is, however, much less pronounced on Ace-AMP1 than on the thionin.

TABLE 2

Antifungal activity of Ace-AMP1, Rs-nsLTP, Zm-nsLTP and Ta-nsLTP on different phytopathogenic fungi

| | IC$_{50}$ (μg/ml) | | | | | | | |
|---|---|---|---|---|---|---|---|---|
| | Ace-AMP1 | | Rs-nsLTP | | Zm-nsLTP | | Ta-nsLTP | |
| FUNGUS | SMF– | SMF+ | SMF– | SMF+ | SMF– | SMF+ | SMF– | SMF+ |
| A brassicola | 2.5 | 1.5 | 48 | 500 | >200 | >200 | >200 | >200 |
| A pisi | 1.0 | 10.0 | 41 | 700 | >200 | >200 | >200 | >200 |
| B cinerea | 3.0 | 7.0 | 45 | 680 | nd | nd | nd | nd |
| C lindemuthianum | 1.5 | 1.5 | 25 | >1000 | >200 | >200 | >200 | >200 |
| F culmorum | 6.0 | 10.0 | 20 | 520 | 200 | >200 | >200 | >200 |
| F oxysporum pisi | 3.5 | 4.0 | 58 | 900 | 200 | >200 | >200 | >200 |
| F oxysporum lycopersici | 3.0 | 10.0 | 54 | >1000 | 200 | >200 | >200 | >200 |
| N haematococca | 3.5 | 7.0 | 100 | >1000 | 60 | >200 | >200 | >200 |
| P betae | 1.5 | 7.0 | 18 | 750 | 150 | >200 | >200 | >200 |
| P tritici-repentis | 3.0 | 3.5 | nd | nd | nd | nd | nd | nd |
| P oryzae | 3.0 | 7.0 | 10 | >1000 | nd | nd | nd | nd |
| V dahliae | 0.25 | 0.5 | 7 | 135 | 200 | >200 | >200 | >200 |

(nd = not determined)

TABLE 3

Antifungal activity of Ace-AMP1, Ac-AMP1 and β-purothionin on *Fusarium culmorum* in synthetic medium supplemented with different cations

| | IC50 (μg/ml) | | | | | | |
|---|---|---|---|---|---|---|---|
| | SMF | +50 mM K+ | +50 mM Na+ | +50 mM NH4+ | +5 mM Mg2+ | +5 mM Ba2+ | +5 mM Ca2+ |
| Ace-AMP1 | 3 | 2 | 2 | 1.5 | 2 | 2 | 6 |
| Ac-AMP1 | 4 | 100 | 100 | 50 | >200 | >200 | >200 |
| β-puro-thionin | 4 | 2 | 3 | 2 | 2 | 2.5 | 35 |

EXAMPLE 8

Anti-bacterial and anti-yeast activity of Ace-AMP1

The purified protein was assessed for its effect on the growth of the following bacteria: *Bacillus megaterium* ATCC 13632, *Sarcina lutea* ATCC 9342, *Agrobacterium tumefaciens* LMG 188, *Alcaligenes eutrophus* LMG 1195, *Azospirillum brasilense* ATCC 29145, *Erwinia carotovora* subsp carotovora LMG2458, *Escherichia coli* strain HB101, *Pseudomonas solanacearum* LMG 2293, *Pseudomonas syringae* pv tabaci LMG 5192 and *Xanthomonas campestris* pv campestris LMG 582. It was also assessed for its effect on the growth of *Saccharomyces cerevisiae* strain Sp1. Bioassays were carried out as described in Example 1. The results are summarised in Table 4.

TABLE 4

Activity of Ace-AMP1, Rs-nsLTP, Zm-nsLTP, Ta-nsLTP on bacteria and yeast

| | IC50 (µg/ml) | | | |
|---|---|---|---|---|
| MICROORGANISM | Ace-AMP1 | Rs-nsLTP | Zm-nsLTP | Ta-nsLTP |
| B megaterium | 0.8 | 20 | 60 | >200 |
| S lutea | 8.0 | >200 | >200 | >200 |
| A tumefaciens | >200 | nd | nd | nd |
| A eutrophus | >200 | nd | nd | nd |
| A brasilense | >200 | nd | nd | nd |
| E carotovoza | >200 | >200 | >200 | >200 |
| E coli | >200 | nd | nd | nd |
| P solanacearum | >200 | nd | nd | nd |
| P syringae | >100 | >200 | >200 | >200 |
| X campestris | >100 | >200 | >200 | >200 |
| S cerevisiae | >200 | nd | nd | nd | nd = not determined

Ace-AMP1 inhibits growth of both Gram positive bacteria tested (*B megaterium* and *S lutea*) but has little or no effect on any of the eight different Gram negative bacteria which were tested or on the yeast *S cerevisiae*. Rs-nsLTP and Zm-nsLTP are only inhibitory to *B megaterium*, but are at least 10-fold less active on this bacterium than Ace-AMP1. The ns-LTPs isolated from barley leaves (including CW18 and CW21, see FIG. 3) have been reported to inhibit growth of the Gram positive bacterium *Clavibacter michiganensis* subsp sepedonicus and the Gram negative bacterium *P solanacearum* (Molina et al, 1993, FEBS Lett, 316:119–122).

EXAMPLE 9

PCR-based cloning of the 5' and 3' parts of Ace-AMP1 cDNA

Total RNA was extracted from a mixture of immature seeds collected 15, 21 and 30 days post anthesis.

The 3' part of Ace-AMP1 cDNA was cloned as follows. Total RNA (1 µg) was reverse transcribed in a 30 µl reaction mixture containing 12 units of avian myeloblastosis virus reverse transcriptase (Boehringer Mannheim), appropriate buffer constituents (Sambrook et al, 1989, Molecular Cloning, Cold Spring Harbor Laboratory Press) and 10 pmol of a modified oligo-dT primer (primer OWB114, see Table 5) and incubated for 30 min at 52° C. A fraction of the reverse transcription reaction (0.5 µl) was transferred to a 25 µl PCR reaction mixture containing 5 pmol of the antisense primer OWB114, 5 pmol of the sense primer OWB111 (a degenerated primer corresponding to an internal amino acid sequence of Ace-AMP1, namely PRFQNIP), 5 nmol dNTPs, 0.5 units of Taq polymerase and Taq polymerase buffer constituents (Sambrook et al, 1989, Molecular Cloning, Cold Spring Harbor Laboratory Press). Temperature cycling for PCR was done according to standard conditions (Sambrook et al., 1989, Molecular Cloning, Cold Spring Harbor Laboratory Press) using a primer annealing temperature of 55° C. PCR reaction products were analysed by agarose gel electrophoresis and a band of about 400 bp (that was absent from control PCR reactions containing the same template but only one of both primers) was isolated using a Prep-a-Gene kit (Biorad) according to the manufacturers instructions. The PCR product was digested with XbaI, subcloned into the plasmid pEMBL18+ (Boehringer Mannheim) and the insert sequenced on an ALF automated sequencer (Pharmacia) using the Autoread sequencing kit (Pharmacia) with fluoresceine-labelled M13 forward and reverse primers.

The 5' part of the Ace-AMP1 cDNA was cloned as follows. Total RNA was reverse transcribed as described above using either OWB114 or OWB133 (an Ace-AMP1 specific primer, derived from the nucleotide sequence of the 3' part of Ace-AMP1 cDNA) as a primer. Excess primer was removed by gel filtration over a Chromaspin+TE-100 (Clontech) column equilibrated in 10 mM Tris, 1 mM EDTA, 300 mM NaCl, 0.05% (w/v) SDS (pH 8). RNA was subsequently removed by alkaline hydrolysis, the ssDNA was ethanol precipitated as described by Delort et al (1989, Nucl Acids Res, 17:6439–6448), and finally redissolved in 10 µl distilled water. The 3' end of these ssDNA preparations (corresponding to the 5' end of the mRNA) were ligated to the oligonucleotide OWB116 which was synthesized with a phosphate group at its 5' end (to allow for ligation to the ssDNA) and an amino group at its 3' end (to avoid primer self-ligation). The ssDNA ligation reaction mixture (30 µl) contained 5 pmol of primer OWB116, 2.5 µl of ssDNA (see above), 10 units of T4 RNA ligase (New England Biolabs) and T4 RNA ligase buffer constituents (Tessier et al, 1986, Anal Biochem, 158:171–178), and incubation was done at 22° C. for 16 h. A fraction (0.1 µl) of the ssDNA ligation mixture was transferred to a 25 µl PCR reaction mixture containing 5 nmol of primer OWB117 (which is partially complementary to OWB116), 5 mmol of dNTPs, 1.25 units of Taq polymerase and Taq polymerase buffer constituents. After 5 PCR cycles with an annealing temperature of 60° C., 25 pmol of an Ace-AMP1-specific primer (OWB132, corresponding to a position on Ace-AMP1 cDNA immediately upstream of that of OW133) was added to the reaction mixture and 30 additional PCR cycles with an annealing temperature of 55° C. were carried out. A PCR product of about 400 bp which was not present in single primer PCR controls was gel-purified as described above. The same 400 bp PCR band was obtained irrespective of whether OWB133 or OWB114 were used in the first strand synthesis. This PCR product was BamHI-digested, subcloned into pEMBL18+ and the nucleotide sequence of the insert determined as described above.

By combining the nucleotide sequences of the 5' and 3' parts (which overlapped by 38 nucleotides) a 686 bp sequence was obtained that corresponds to full length Ace-nsLTP cDNA.

Ace-AMP1 cDNA contains a 396 bp open reading frame coding for 132 amino acids, a 36 bp 5' leader sequence and a 3' untranslated region of 232 bp up to the poly (A+) tail (FIGS. 4A and 4B). Analysis of the coding region reveals the presence of a putative signal peptide of 27 amino acids. The predicted signal peptide cleavage site (indicated by an arrow in FIGS. 4A and 4B) is in agreement with the rules of von Heijne (1986, Nucl Acids Res, 14:4683–4690) and with the observation that most mature plant nsLTPs have a cysteine at positions 4 and a valine at position 7. The amino acid sequence between amino acids 37 and 120 of the coding region (underlined in FIGS. 4A and 4B) identical to the amino acid sequence determined experimentally for mature Ace-AMP1. The cDNA derived coding region predicted that mature Ace-AMP1 has 9 additional amino acids at the N-terminus relative to the sequence determined in Example 5. This sequence could not be determined experimentally due to the presence of a blocked N-terminal amino acid in mature Ace-AMP1. Furthermore, the translation product of Ace-AMP1 mRNA has 12 amino acids at its carboxyl-terminus which are absent from mature Ace-AMP1. This carboxyl-terminal propeptide is rich in hydrophobic and acidic residues, a characteristic feature of carboxyl-terminal propeptides present in the precursors of vacuolar plant proteins (Nakamura and Matsuoka, 1993, Plant Physiol, 101:1–5).

Such carboxyl-terminal propeptides have in a number of cases been demonstrated to be determinants for targetting the protein to the vacuole (Bednarek and Raikhel, 1991, Plant Cell, 3,:1195–1206; Neuhaus et al, 1991, Proc Natl Acad Sci USA, 88:10362–10366). All nsLTP-like proteins have been shown to be translated as preproteins, which deviates from the preproprotein structure found in the case of Ace-AMP1 (Arondel and Kader, 1990, Experientia, 46:579–585; Madrid and von Wettstein, 1991, Plant Physiol Biochem, 29:705–711).

TABLE 5

Oligonucleotides used for Ace-AMP1 cDNA cloning
Name Sequence
OWB114 (SEQ ID NO: 17) 5'-CCACTCTAGAGAATTCA CCTTTTTTTTTTTTTTTTTTTTT-3'
OWB116 (SEQ ID NO: 18) 5'-AGAATTCGCATTGCATC GGATCCATGATCGAT-3'
OWB117 (SEQ ID NO: 19) 5'-ATCGATCATGGATCC GATGCAATGC-3'
OWB111 (SEQ ID NO: 20) 5'-AATTCTAGACCNMGNTT YCARAAYATHCC-3'
OWB132 (SEQ ID NO: 21) 5'-ATCGGATCCGAATTCGT GTTGCGACAATCACGAGG-3'
OWB133 (SEQ ID NO: 22) 5'-ATCGGATCCGAATTCAG GACGAACAAAGGTGTTGC-3'
OWB158 (SEQ ID NO: 23) 5'-TAAGGTACCATGGTTCG CGTTGTATC-3'
OWB159 (SEQ ID NO: 24) 5'-TAAGGATCCTTCAGTTA ATCCTGCCGCATTGAATTCG-3'
OWB160 (SEQ ID NO: 25) 5'-TAAGGATCCCTTCATTC CTCAGCGTCCAAG-3'

The following oligonucleotides have a sense orientation relative to Ace-AMP1 mRNA: OWB117, OWB111, OWB158. The remaining oligonucleotides (OWB114, OWB116, OWB132, OWB133, OWB159, OWB160) have an antisense orientation relative to Ace-AMP1 mRNA. The position of each oligonucleotide relative to the Ace-AMP1 cDNA nucleotide sequence is as follows:

OWB114 poly(A⁺) tail
OWB116 5'-end
OWB117 5'end
OWB111 307–326
OWB132 325–344
OWB133 338–354
OWB158 35–53
OWB159 372–396
OWB160 417–437.

Restriction sites in the oligonucleotides are underlined in Table 5. In OWB116, the 5'OH at the 5' end is phosphorylated and the 3'OH at the 3' end is aminated. The sequence of OWB117 is complementary to nucleotides 8–32 of OWB116. In OWB111: N=G,A,T,C; H=A,C,T; M=A,C; Y=C,T; R=A,G.

EXAMPLE 10

Construction of an expression vector

Total onion seed RNA was reverse translated using primer OWB114 as described in example 9. Fractions (0.5 μl) of the reaction mixture were used in PCR amplification reactions under standard conditions (Sambrook et al, 1989, Molecular Cloning, Cold Spring Harbor Laboratory Press) using either the primer combination OWB158–OWB159 at a primer annealing temperature of 65° C. or the primers OWB158–OWB160 at a primer annealing temperature of 55° C. Primer OWB158 introduces a KpnI site immediately upstream of the natural NcoI site of Ace-AMP1 cDNA (which encompasses the start codon), primer OWB159 introduces a stop codon and a BamHI site behind the codon of amino acid 120 (the last amino acid of mature Ace-AMP1), and primer OWB160 introduces a BamHI site behind the natural stop codon of Ace-AMP1. The resulting OWB158–OWB159 and OWB158–OWB160 amplification products were digested with KpnI and BamHI and subcloned into the corresponding sites of plasmid pBluescript II SK—to yield plasmids pAce2 and pAce1, respectively. The inserts were verified by nucleotide sequencing. The inserts of plasmids pAce1 and pAce2 were isolated by digestion with NcoI and SacI and subsequently ligated into the corresponding sites of the expression vector pBI505 (Datla et al, 1993, Plant Science, 94:139–149), thus creating plasmids pAce3 and pAce4, respectively. In the expression vector pAce3, the coding region of Ace-AMP1 is flanked at its 5 end by the strong constitutive promoter of the 35S RNA of cauliflower mosaic virus with a duplicated enhancer element (to allow for high transcriptional activity, Kay et al, 1987, Science, 236:1299–1302) and the 5' leader sequence of the alfalfa mosaic virus (to allow for high translational activity, Datla et al, 1993, Plant Science, 94:139–149). The coding region of the Ace-AMP1 cDNA is flanked at its 3' end by the polyadenylation sequence of the *Agrobacterium tumefaciens* nopaline synthase gene (Bevan et al, 1983, Nature, 304:184–187). Vector pAce4 is identical to pAce3 except that the coding region lacks the domain encoding the 12 carboxyl-terminal amino acids of the propeptide.

EXAMPLE 11

Construction of plant transformation vectors

The expression vectors pAce3 and pAce4 described in example 10 were digested with HindIII and SacI and the fragments containing the Ace-AMP1 expression cassettes were subcloned into the HindIII-SacI digested plant transformation vector pGPTV-KAN (Becker et al, 1992, Plant Mol Biol, 20:1195–1197) yielding plant transformation vectors pFAJ3033 and pFAJ3034, respectively. A schematic representation of these vectors is shown in FIGS. 5A and 5B.

Figure 5A:
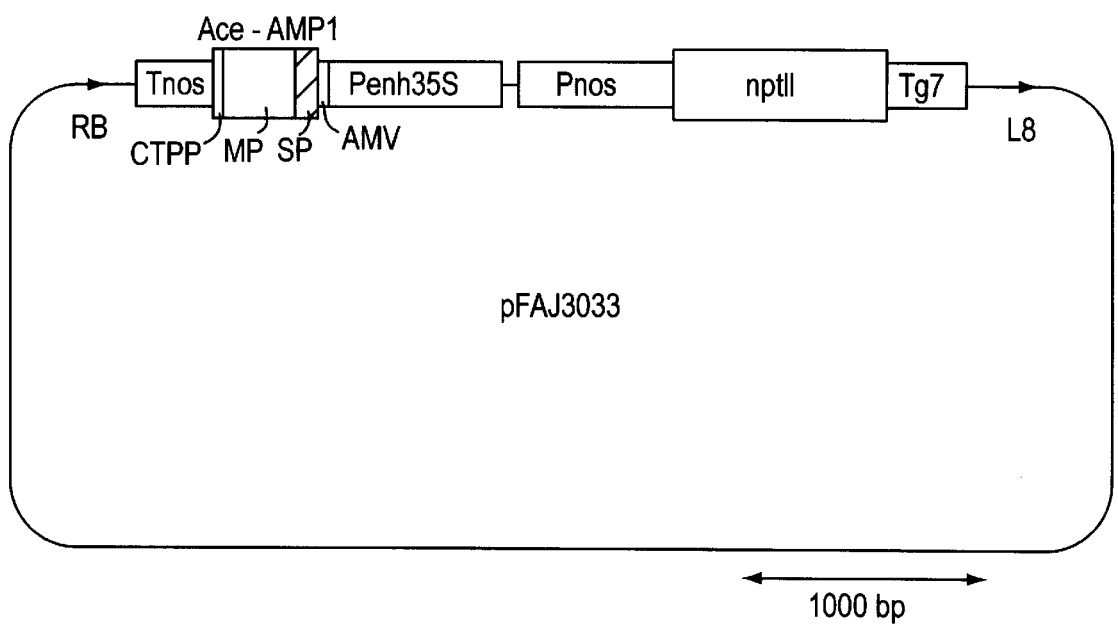
FIGS. 5A and 5B are diagrams of the vectors pFAJ3033 and pFAJ3034.
Figure 5B:
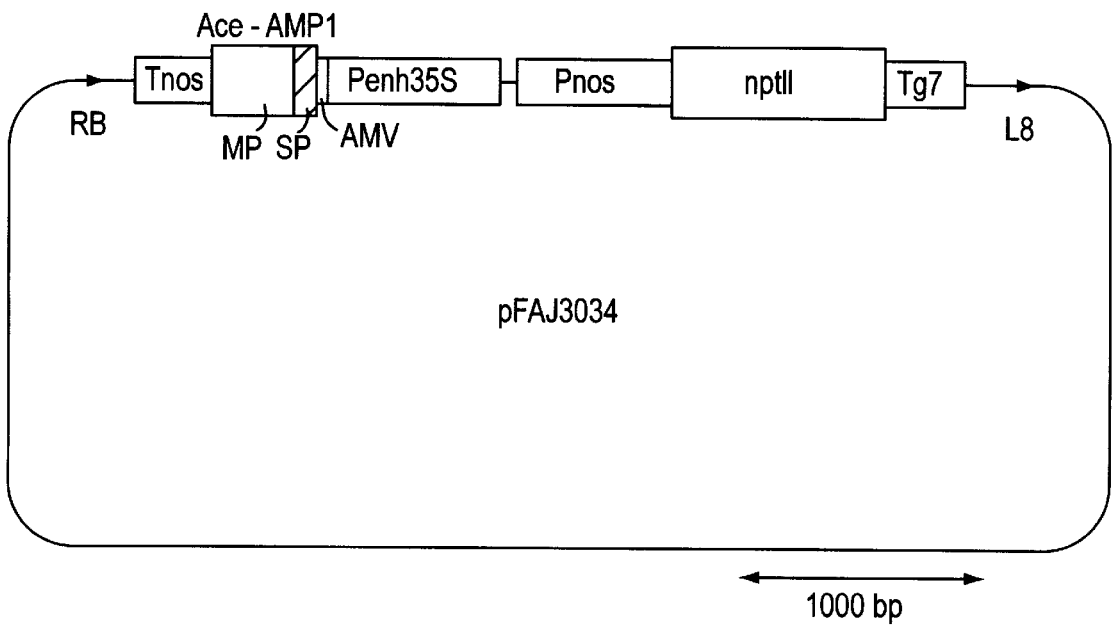

The symbols used in FIGS. 5A and 5B are as follows:
RB: right border of T-DNA
LB: left border of T-DNA
Tnos: terminator of T-DNA nopaline synthase gene
CTPP: carboxy-terminal propeptide domain of Ace-AMP1 cDNA
MP: mature protein domain of Ace-AMP1 cDNA
SP: signal peptide domain of Ace-AMP1 cDNA
AMV: alfalfa mosaic virus 5' leader sequence
Penh35S: promoter of 35S RNA of cauliflower mosaic virus with duplicated enhancer region Pnos: promoter of T-DNA nopaline synthase gene
nptII: coding region of neomycin phosphotransferase II gene
Tg7: terminator of T-DNA gene 7

EXAMPLE 12

Plant Transformation

The disarmed *Agrobacterium tumefaciens* strain LBA4404 (pAL4404) (Hoekema et al, 1983, Nature 303, 179–180) is transformed with the transformation vector using the method of de Framond et al (BioTechnology, 1:262–269).

Tobacco transformation is carried out using leaf discs of *Nicotiana tabacum* Samsun based on the method of Horsch et al (1985, Science, 227:1229–1231) and co-culturing with Agrobacterium strains containing pFAJ3033 or pFAJ3034. Co-cultivation is carried out under selection pressure of 100 μg/ml kanamycin. Transgenic plants are regenerated on media containing 100 μg/ml kanamycin. These transgenic plants may be analysed for expression of the newly introduced genes using standard western blotting techniques. Plants capable of constitutive expression of the introduced genes may be selected and self-pollinated to give seed. F1 seedlings of the transgenic plants may be further analysed for increased resistance to plant pathogens.

---

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
    ( A ) LENGTH: 93 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: Ace-AMP1

( x i ) SEQUENCE DESCRIPTION: SEQ ID NO: 1:

```
Gln Asn Ile Cys Pro Arg Val Asn Arg Ile Val Thr Pro Cys Val Ala
 1               5                  10                  15
Tyr Gly Leu Gly Arg Ala Pro Ile Ala Pro Cys Cys Arg Ala Leu Asn
            20                  25                  30
Asp Leu Arg Phe Val Asn Thr Arg Asn Leu Arg Arg Ala Ala Cys Arg
        35                  40                  45
Cys Leu Val Gly Val Val Asn Arg Asn Pro Gly Leu Arg Arg Asn Pro
    50                  55                  60
Arg Phe Gln Asn Ile Pro Arg Asp Cys Arg Asn Thr Phe Val Arg Pro
65                  70                  75                  80
Phe Trp Trp Arg Pro Arg Ile Gln Cys Gly Arg Ile Asn
                85                  90
```

( 2 ) INFORMATION FOR SEQ ID NO: 2:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: Rs-nsLTP ( x i ) SEQUENCE DESCRIPTION: SEQ ID NO: 2:

```
Ala Leu Ser Cys Gly Thr Val Asn Ser Leu Asn Ala Ala Cys Ile Gly
 1               5                  10                  15
Tyr Leu Thr Gln Asn Ala Pro Leu Ala Arg Gly Cys Cys Thr Gly Val
            20                  25                  30
Thr Asn Leu Asn Asn Met Ala Thr Thr Pro
```

35 40

( 2 ) INFORMATION FOR SEQ ID NO: 3:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: So-nsLTP ( x i ) SEQUENCE DESCRIPTION: SEQ ID NO: 3:

```
Gly  Ile  Thr  Cys  Gly  Met  Val  Ser  Ser  Lys  Leu  Ala  Pro  Cys  Ile  Gly
 1               5                        10                       15
Ile  Leu  Lys  Gly  Gly  Pro  Leu  Gly  Gly  Cys  Cys  Gly  Gly  Ile  Lys
               20                       25                       30
Ala  Leu  Asn  Ala  Ala  Ala  Ala  Thr  Thr  Pro  Asp  Arg  Lys  Thr  Ala  Cys
               35                       40                       45
Asn  Cys  Leu  Lys  Ser  Ala  Ala  Asn  Ala  Ile  Lys  Gly  Ile  Asn  Tyr  Gly
      50                       55                       60
Lys  Ala  Ala  Gly  Leu  Pro  Gly  Met  Cys  Gly  Val  His  Ile  Pro  Tyr  Ala
65                        70                       75                       80
Ile  Ser  Pro  Ser  Thr  Asn  Cys  Asn  Ala  Val  His
                    85                       90
```

( 2 ) INFORMATION FOR SEQ ID NO: 4:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: EP2

( x i ) SEQUENCE DESCRIPTION: SEQ ID NO: 4:

```
Val  Leu  Thr  Cys  Gly  Gln  Val  Thr  Gly  Ala  Leu  Ala  Pro  Cys  Leu  Gly
 1               5                        10                       15
Tyr  Leu  Arg  Ser  Gln  Val  Asn  Val  Pro  Val  Pro  Leu  Thr  Cys  Cys  Asn
               20                       25                       30
Val  Val  Arg  Gly  Leu  Asn  Asn  Ala  Ala  Arg  Thr  Thr  Leu  Asp  Arg  Lys
               35                       40                       45
Thr  Ala  Cys  Gly  Cys  Leu  Lys  Gln  Thr  Ala  Asn  Ala  Val  Thr  Gly  Leu
      50                       55                       60
Asn  Leu  Asn  Ala  Ala  Ala  Gly  Leu  Pro  Ala  Arg  Cys  Gly  Val  Asn  Ile
65                        70                       75                       80
Pro  Tyr  Lys  Ile  Ser  Pro  Thr  Thr  Asp  Cys  Asn  Arg  Val  Val
                    85                       90
```

( 2 ) INFORMATION FOR SEQ ID NO: 5:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
    ( A ) ORGANISM: TobLTP ( x i ) SEQUENCE DESCRIPTION: SEQ ID NO: 5:

```
Ala Leu Ser Cys Gly Gln Val Gln Ser Gly Leu Ala Pro Cys Leu Pro
 1               5                  10                  15
Tyr Leu Gln Gly Arg Gly Pro Leu Gly Ser Cys Cys Gly Gly Val Lys
            20                  25                  30
Gly Leu Leu Gly Ala Ala Lys Ser Leu Ser Asp Arg Lys Thr Ala Cys
            35                  40                  45
Ile Cys Leu Lys Ser Ala Ala Asn Ala Ile Lys Gly Ile Asp Met Gly
     50                  55                  60
Lys Ala Ala Gly Leu Pro Gly Ala Cys Gly Val Asn Ile Pro Tyr Lys
 65              70                  75                  80
Ile Ser Pro Ser Thr Asp Cys Ser Lys Val Gln
                 85                  90
```

( 2 ) INFORMATION FOR SEQ ID NO: 6:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Le-nsLTP ( x i ) SEQUENCE DESCRIPTION: SEQ ID NO: 6:

```
Ala Leu Thr Cys Gly Gln Val Thr Ala Gly Leu Ala Pro Cys Leu Pro
 1               5                  10                  15
Tyr Leu Gln Gly Arg Gly Pro Leu Gly Gly Cys Cys Gly Gly Val Lys
            20                  25                  30
Asn Leu Leu Gly Ser Ala Lys Thr Thr Ala Asp Arg Lys Thr Ala Cys
            35                  40                  45
Thr Cys Leu Lys Ser Ala Ala Asn Ala Ile Lys Gly Ile Asp Leu Asn
     50                  55                  60
Lys Ala Ala Gly Ile Pro Ser Val Cys Lys Val Asn Ile Pro Tyr Lys
 65              70                  75                  80
Ile Ser Pro Ser Thr Asp Cys Ser Thr Val Gln
                 85                  90
```

( 2 ) INFORMATION FOR SEQ ID NO: 7:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: CB-A ( x i ) SEQUENCE DESCRIPTION: SEQ ID NO: 7:

```
Val Asp Cys Gly Gln Val Asn Ser Ser Leu Ala Ser Cys Ile Pro Phe
 1               5                  10                  15
Leu Thr Gly Gly Val Ala Ser Pro Ser Ala Ser Cys Cys Ala Gly Val
            20                  25                  30
```

```
Gln  Asn  Leu  Lys  Thr  Leu  Ala  Pro  Thr  Ser  Ala  Asp  Arg  Arg  Ala  Ala
          35                      40                     45

Cys  Glu  Cys  Ile  Lys  Ala  Ala  Ala  Arg  Phe  Pro  Thr  Ile  Lys  Gln
     50                      55                 60

Asp  Ala  Ala  Ser  Ser  Leu  Pro  Lys  Lys  Cys  Gly  Val  Asp  Ile  Asn  Ile
65                       70                   75                            80

Pro  Ile  Ser  Lys  Thr  Thr  Asn  Cys  Gln  Ala  Ile  Asn
               85                       90
```

(2) INFORMATION FOR SEQ ID NO: 8:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: CB-C (xi) SEQUENCE DESCRIPTION: SEQ ID NO: 8:

```
Val  Asn  Cys  Gly  Gln  Val  Asn  Lys  Ala  Leu  Ser  Ser  Cys  Val  Pro  Phe
1                        5                        10                      15

Leu  Thr  Gly  Phe  Asp  Thr  Thr  Pro  Ser  Leu  Thr  Cys  Cys  Ala  Gly  Val
               20                      25                      30

Met  Leu  Leu  Lys  Arg  Leu  Ala  Pro  Thr  Val  Lys  Asp  Lys  Arg  Ile  Ala
          35                      40                     45

Cys  Glu  Cys  Val  Lys  Thr  Ala  Ala  Ala  Arg  Tyr  Pro  Asn  Ile  Arg  Glu
     50                      55                 60

Asp  Ala  Ala  Ser  Ser  Leu  Pro  Tyr  Lys  Cys  Gly  Val  Val  Ile  Asn  Val
65                       70                   75                            80

Pro  Ile  Ser  Lys  Thr  Thr  Asn  Cys  His  Glu  Ile  Asn
               85                       90
```

(2) INFORMATION FOR SEQ ID NO: 9:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: CB-B (xi) SEQUENCE DESCRIPTION: SEQ ID NO: 9:

```
Ala  Val  Pro  Cys  Ser  Thr  Val  Asp  Met  L ( 2 ) INFORMATION FOR SEQ ID NO: 10:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: PAPI ( x i ) SEQUENCE DESCRIPTION: SEQ ID NO: 10:

```
Ala Leu Asn Cys Gly Gln Val Asp Ser Lys Met Lys Pro Cys Leu Thr
 1               5                  10                  15
Tyr Val Gln Gly Gly Pro Gly Gly Pro Ser Gly Leu Cys Cys Asn Gly
            20                  25                  30
Val Arg Asp Leu His Asn Gln Ala Gln Ser Ser Gly Asp Arg Gln Thr
        35                  40                  45
Val Cys Asn Cys Leu Lys Gly Ile Ala Arg Gly Ile His Asn Leu Asn
    50                  55                  60
Leu Asn Asn Ala Ala Ser Ile Pro Ser Lys Cys Asn Val Asn Val Pro
65                  70                  75                  80
Tyr Thr Ile Ser Pro Asp Ile Asp Cys Ser Arg Ile Tyr
                85                  90
```

( 2 ) INFORMATION FOR SEQ ID NO: 11:

( i ) SEQUENCE CHARACTERISTICS:
        ( A ) LENGTH: 90 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: CW18

( x i ) SEQUENCE DESCRIPTION: SEQ ID NO: 11:

```
Ala Ile Thr Cys Gly Gln Val Ser Ser Ala Leu Gly Pro Cys Ala Ala
 1               5                  10                  15
Tyr Ala Lys Gly Ser Ser Thr Ser Pro Ser Ala Gly Cys Cys Ser Gly
            20                  25                  30
Val Lys Arg Leu Ala Gly Leu Ala Arg Ser Thr Ala Asp Lys Gln Ala
        35                  40                  45
Thr Cys Arg Cys Leu Lys Ser Val Ala Gly Ala Tyr Asn Ala Gly Arg
    50                  55                  60
Ala Ala Gly Ile Pro Ser Arg Cys Gly Val Ser Val Pro Tyr Thr Ile
65                  70                  75                  80
Ser Ala Ser Val Asp Cys Ser Lys Ile His
                85                  90
```

( 2 ) INFORMATION FOR SEQ ID NO: 12:

( i ) SEQUENCE CHARACTERISTICS:
        ( A ) LENGTH: 90 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:

(A) ORGANISM: CW21

(xi) SEQUENCE DESCRIPTION: SEQ ID NO: 12:

| Ala | Ile | Ser | Cys | Gly | Gln | Val | Ser | Ser | Ala | Leu | Ser | Pro | Cys | Ile | Ser |
|---|---|---|---|---|---|---|---|---|---|---|---|---|---|---|---|
| 1 | | | | 5 | | | | | 10 | | | | | 15 | |
| Tyr | Ala | Arg | Gly | Asn | Gly | Ala | Lys | Pro | Pro | Ala | Ala | Cys | Cys | Ser | Gly |
| | | | 20 | | | | | 25 | | | | | 30 | | |
| Tyr | Lys | Arg | Leu | Ala | Gly | Ala | Ala | Gln | Ser | Thr | Ala | Asp | Lys | Gln | Ala |
| | | | 35 | | | | 40 | | | | | 45 | | | |
| Thr | Cys | Arg | Cys | Ile | Lys | Ser | Ala | Ala | Gly | Gly | Leu | Asn | Ala | Gly | Lys |
| | | 50 | | | | | 55 | | | | | 60 | | | |
| Ala | Ala | Gly | Ile | Pro | Ser | Met | Cys | Gly | Val | Ser | Val | Pro | Tyr | Ala | Ile |
| 65 | | | | | 70 | | | | | 75 | | | | | 80 |
| Ser | Ala | Ser | Val | Asp | Cys | Ser | Lys | Ile | Arg | | | | | | |
| | | | | 85 | | | | | 90 | | | | | | |

(2) INFORMATION FOR SEQ ID NO: 13:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ta-nsLTP (xi) SEQUENCE DESCRIPTION: SEQ ID NO: 13:

| Ile | Asp | Cys | Gly | His | Val | Asp | Ser | Leu | Val | Arg | Pro | Cys | Leu | Ser | Tyr |
|---|---|---|---|---|---|---|---|---|---|---|---|---|---|---|---|
| 1 | | | | 5 | | | | | 10 | | | | | 15 | |
| Val | Gln | Gly | Gly | Pro | Gly | Pro | Ser | Gln | Cys | Cys | Asp | Gly | Val | Lys | |
| | | | 20 | | | | | 25 | | | | | 30 | | |
| Asn | Leu | His | Asn | Gln | Ala | Arg | Ser | Gln | Ser | Asp | Arg | Gln | Ser | Ala | Cys |
| | | | 35 | | | | 40 | | | | | 45 | | | |
| Asn | Cys | Leu | Lys | Gly | Ile | Ala | Arg | Gly | Ile | His | Asn | Leu | Asn | Glu | Asp |
| | | 50 | | | | | 55 | | | | | 60 | | | |
| Asn | Ala | Arg | Ser | Ile | Pro | Pro | Lys | Cys | Gly | Val | Asn | Leu | Pro | Tyr | Thr |
| 65 | | | | | 70 | | | | | 75 | | | | | 80 |
| Ile | Ser | Leu | Asn | Ile | Asp | Cys | Ser | Arg | Val | | | | | | |
| | | | | 85 | | | | | 90 | | | | | | |

(2) INFORMATION FOR SEQ ID NO: 14:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Zm-nsLTP (xi) SEQUENCE DESCRIPTION: SEQ ID NO: 14:

| Ala | Ile | Ser | Cys | Gly | Gln | Val | Ala | Ser | Ala | Ile | Ala | Pro | Cys | Ile | Ser |
|---|---|---|---|---|---|---|---|---|---|---|---|---|---|---|---|
| 1 | | | | 5 | | | | | 10 | | | | | 15 | |
| Tyr | Ala | Arg | Gly | Gln | Gly | Ser | Gly | Pro | Ser | Ala | Gly | Cys | Cys | Ser | Gly |
| | | | 20 | | | | | 25 | | | | | 30 | | |
| Val | Arg | Ser | Leu | Asn | Asn | Ala | Ala | Arg | Thr | Thr | Ala | Asp | Arg | Arg | Ala |
| | | | 35 | | | | 40 | | | | | 45 | | | |

```
Ala Cys Asn Cys Leu Lys Asn Ala Ala Gly Val Ser Gly Leu Asn
        50                  55                  60

Ala Gly Asn Ala Ala Ser Ile Pro Ser Lys Cys Gly Val Ser Ile Pro
 65              70                  75                      80

Tyr Thr Ile Ser Thr Ser Thr Asp Cys Ser Arg Val Asn
                 85                  90
```

( 2 ) INFORMATION FOR SEQ ID NO: 15:

( i ) SEQUENCE CHARACTERISTICS:
        ( A ) LENGTH: 686 base pairs
        ( B ) TYPE: nucleic acid
        ( C ) STRANDEDNESS: single
        ( D ) TOPOLOGY: linear
            ( 1 1 1 MOLECULE TYPE: cDNA ( v i ) ORIGINAL SOURCE:
        ( A ) ORGANISM: Ace-AMP1

( x i ) SEQUENCE DESCRIPTION: SEQ ID NO: 15:

```
AACGAAAATT ACGAAATTAC ATCAATATCT CGAGCCATGG TTCGCGTTGT ATCTTTACTT   60
GCAGCATCGA CCTTCATACT GTTGATTATG ATAATCAGCA GTCCGTATGC ARATAGTCAG  120
AACATATGCC CAAGGGTTAA TCGAATTGTG ACACCCTGTG TGGCCTACGG ACTCGGAAGG  180
GCACCAATCG CCCCATGCTG CAGAGCCCTG AACGATCTAC GGTTTGTGAA TACTAGAAAC  240
CTACGACGTG CTGCATGCCG CTGCCTCGTA GGGGTAGTGA ACCGGAACCC CGGTCTGAGA  300
CGAAACCCTA GATTTCAGAA CATTCCTCGT GATTGTCGCA ACACCTTTGT TCGTCCCTTC  360
TGGTGGCGTC CAAGAATTCA ATGCGGCAGG ATTAACCTTA CGGATAAGCT TATATACTTG  420
GACGCTGAGG AATGAAGACT AGGCTCTACT GTTATGCACT ATAGTTTATA GTATATATAC  480
TAAATAAAAC AGTATGTGCT GTATAATTTG CAATATGGAC TTATTTATAG CAAGTCCTAA  540
TGGTGTCTGC TACTTGGGTC CAGCATTGAG CACTATATAG GCACTATATA GGGTACTATG  600
GGCTGATTAT GATGTCAACG GCGGTACTTT ATCTTACATA AATAAATAAT GGGTTTATCT  660
TGCTTGAAAA AAAAAAAAAA AAAAAA                                      686
```

( 2 ) INFORMATION FOR SEQ ID NO: 16:

( i ) SEQUENCE CHARACTERISTICS:
        ( A ) LENGTH: 132 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Ace-AMP1 (translated)

( x i ) SEQUENCE DESCRIPTION: SEQ ID NO: 16:

```
Met Val Arg Val Val Ser Leu Leu Ala Ala Ser Thr Phe Ile Leu Leu
 1               5                  10                  15

Ile Met Ile Ile Ser Ser Pro Tyr Ala Asn Ser Gln Asn Ile Cys Pro
             20                  25                  30

Arg Val Asn Arg Ile Val Thr Pro Cys Val Ala Tyr Gly Leu Gly Arg
             35                  40                  45

Ala Pro Ile Ala Pro Cys Cys Arg Ala Leu Asn Asp Leu Arg Phe Val
         50              55                  60

Asn Thr Arg Asn Leu Arg Arg Ala Ala Cys Arg Cys Leu Val Gly Val
 65              70                  75                      80
```

```
Val  Asn  Arg  Asn  Pro  Gly  Leu  Arg  Arg  Asn  Pro  Arg  Phe  Gln  Asn  Ile
                    85                       90                      95

Pro  Arg  Asp  Cys  Arg  Asn  Thr  Phe  Val  Arg  Pro  Phe  Trp  Trp  Arg  Pro
               100                      105                     110

Arg  Ile  Gln  Cys  Gly  Arg  Ile  Asn  Leu  Thr  Asp  Lys  Leu  Ile  Tyr  Leu
          115                      120                     125

Asp  Ala  Glu  Glu
          130
```

( 2 ) INFORMATION FOR SEQ ID NO: 17:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB114

( x i ) SEQUENCE DESCRIPTION: SEQ ID NO: 17:

CCACTCTAGA GAATTCACCT TTTTTTTTTT TTTTTTTT      39

( 2 ) INFORMATION FOR SEQ ID NO: 18:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB116

( x i ) SEQUENCE DESCRIPTION: SEQ ID NO: 18:

AGAATTCGCA TTGCATCGGA TCCATGATCG AT      32

( 2 ) INFORMATION FOR SEQ ID NO: 19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB117

( x i ) SEQUENCE DESCRIPTION: SEQ ID NO: 19:

ATCGATCATG GATCCGATGC AATGC      25

( 2 ) INFORMATION FOR SEQ ID NO: 20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB111

( x i ) SEQUENCE DESCRIPTION: SEQ ID NO: 20:

AATTCTAGAC CNMGNTTYCA RAAYATHCC 29

( 2 ) INFORMATION FOR SEQ ID NO: 21:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: CUNA ( v i ) ORIGINAL SOURCE:
        ( A ) ORGANISM: OWB132

( x i ) SEQUENCE DESCRIPTION: SEQ ID NO: 21:

ATCGGATCCG AATTCGTGTT GCGACAATCA CGAGG 35

( 2 ) INFORMATION FOR SEQ ID NO: 22:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB133

( x i ) SEQUENCE DESCRIPTION: SEQ ID NO: 22:

ATCGGATCCG AATTCAGGAC GAACARAGGT GTTGC 35

( 2 ) INFORMATION FOR SEQ ID NO: 23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB158

( x i ) SEQUENCE DESCRIPTION: SEQ ID NO:23:

TAAGGTACCA TGGTTCGCGT TGTATC 26

( 2 ) INFORMATION FOR SEQ ID NO: 24:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: OWB159

( x i ) SEQUENCE DESCRIPTION: SEQ ID NO: 24:

TAAGGATCCT TCAGTTAATC CTGCCGCATT GAATTCG 37

( 2 ) INFORMATION FOR SEQ ID NO: 25:

( i ) SEQUENCE CHARACTERISTICS:

-continued (A) LENGTH: 30 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: OWB160

(xi) SEQUENCE DESCRIPTION: SEQ ID NO: 25:

TAAGGATCCC TTCATTCCTC AGCGTCCAAG 30

We claim:

1. An antimicrobial protein comprising the amino acid sequence of SEQ. ID. NO: 1.
2. The antimicrobial protein of claim 1 consisting of the amino acid sequence of SEQ. ID. NO: 16.
3. The antimicrobial protein of either claim 1 or claim 2 which is isolated from seeds of the family Alliaceae.
4. The antimicrobial protein of claim 3 which is isolated from seeds of the genus Allium.
5. The antimicrobial protein of claim 4 which is the protein Ace-AMP1.
6. An isolated nucleic acid encoding the antimicrobial protein of either claim 1 or 2.
7. The isolated nucleic acid of claim 6 wherein the sequence of the nucleic acid comprises SEQ. ID. NO: 15.
8. A biological system transformed with the isolated nucleic acid of claim 6.
9. The transformed biological system of claim 8 which is a microorganism.
10. The transformed biological system of claim 8 which is a plant.
11. A method of inhibiting the growth of fungi or bacteria comprising exposing said fungi or bacteria to the antimicrobial protein of either claim 1 or 2.

* * * * *